US009788996B2

(12) United States Patent
Roy et al.

(10) Patent No.: US 9,788,996 B2
(45) Date of Patent: Oct. 17, 2017

(54) OPHTHALMOLOGICAL DEVICE FOR THE TREATMENT OF KERATOCONUS

(71) Applicant: I.A.C.E.R. S.R.L., Venice (IT)

(72) Inventors: Pierre Roy, Paris (FR); Mario Caprara, Venice (IT); Matteo ZEnnaro, Venice (IT)

(73) Assignee: I.A.C.E.R. S.R.L., Venice (IT)

( * ) Notice: Subject to any disclaimer, the term of this patent is extended or adjusted under 35 U.S.C. 154(b) by 164 days.

(21) Appl. No.: 14/904,431

(22) PCT Filed: Jul. 23, 2014

(86) PCT No.: PCT/IB2014/001382
§ 371 (c)(1),
(2) Date: Jan. 12, 2016

(87) PCT Pub. No.: WO2015/015268
PCT Pub. Date: Feb. 5, 2015

(65) Prior Publication Data
US 2016/0143777 A1    May 26, 2016

(30) Foreign Application Priority Data
Jul. 31, 2013 (IT) .............................. VE2013A0043

(51) Int. Cl.
*A61F 9/00* (2006.01)
*A61F 9/013* (2006.01)
(Continued)

(52) U.S. Cl.
CPC ............ *A61F 9/0026* (2013.01); *A61F 9/013* (2013.01); *A61N 1/303* (2013.01); *A61N 5/062* (2013.01);
(Continued)

(58) Field of Classification Search
CPC .. A61B 17/0231; A61F 9/007; A61F 9/00256; A61F 9/013; A61M 1/0058; A61N 1/303; A61N 5/062; A61N 2005/063
See application file for complete search history.

(56) References Cited

U.S. PATENT DOCUMENTS 6,154,671 A * 11/2000 Parel ..................... A61F 9/0017
604/20
6,267,752 B1 7/2001 Svetliza
(Continued)

FOREIGN PATENT DOCUMENTS

WO    WO2012095876 A1    7/2012

*Primary Examiner* — Nathan R Price
*Assistant Examiner* — John Doubrava
(74) *Attorney, Agent, or Firm* — Themis Law

(57) ABSTRACT

An ophthalmological device for the treatment of keratoconus includes a cylindrical reservoir made of a non-conductive material, open at the top and bottom, and formed by two telescopically engaged portions, a lower one open at the bottom and connected to a cylindrical chamber of smaller diameter, also open at the bottom and formed by an external annular chamber that is concentrically arranged around the chamber and is closed at the top, open at the bottom, and adapted to be placed on the eye; a first metallic conductor, housed in the container and connected to a terminal of a DC voltage generator, to the other terminal of which a second metallic conductor is connected; a first conduit provided with a closing device, one end of the first conduit flowing into the annular reservoir, the other end being located externally thereto, whereby vacuum may be applied through the first conduit; and a second conduit provided with a closing device, one end of the second conduit passing through the annular reservoir at its lower edge and flowing into the container, the other end being located externally to the annular reservoir. During irradiation, a hydrating solution is administered from above through the metallic con- (Continued)

ductor that touches the eye and is released through the conduit to avoid the excessive absorption of incident energy by the hydrating solution while maintaining a minimum thickness and constant hydrating solution on the ocular surface.

3 Claims, 1 Drawing Sheet

(51) Int. Cl.
  *A61N 1/30* (2006.01)
  *A61N 5/06* (2006.01)
  *A61M 37/00* (2006.01)
(52) U.S. Cl.
  CPC ..... *A61M 37/00* (2013.01); *A61M 2210/0612* (2013.01); *A61N 2005/063* (2013.01)

(56) References Cited

U.S. PATENT DOCUMENTS

| | | | |
|---|---|---|---|
| 2007/0112295 A1* | 5/2007 | Roy | A61F 9/0017 604/20 |
| 2007/0123814 A1* | 5/2007 | Roy | A61N 1/0424 604/20 |
| 2009/0069798 A1* | 3/2009 | Muller | A61F 9/007 606/33 |
| 2009/0209954 A1 | 8/2009 | Muller et al. | |
| 2010/0057060 A1 | 3/2010 | Herekar | |
| 2011/0301526 A1* | 12/2011 | Moslemy | A61N 1/0444 604/20 |
| 2013/0178821 A1* | 7/2013 | Foschini | A61K 31/525 604/501 |

* cited by examiner

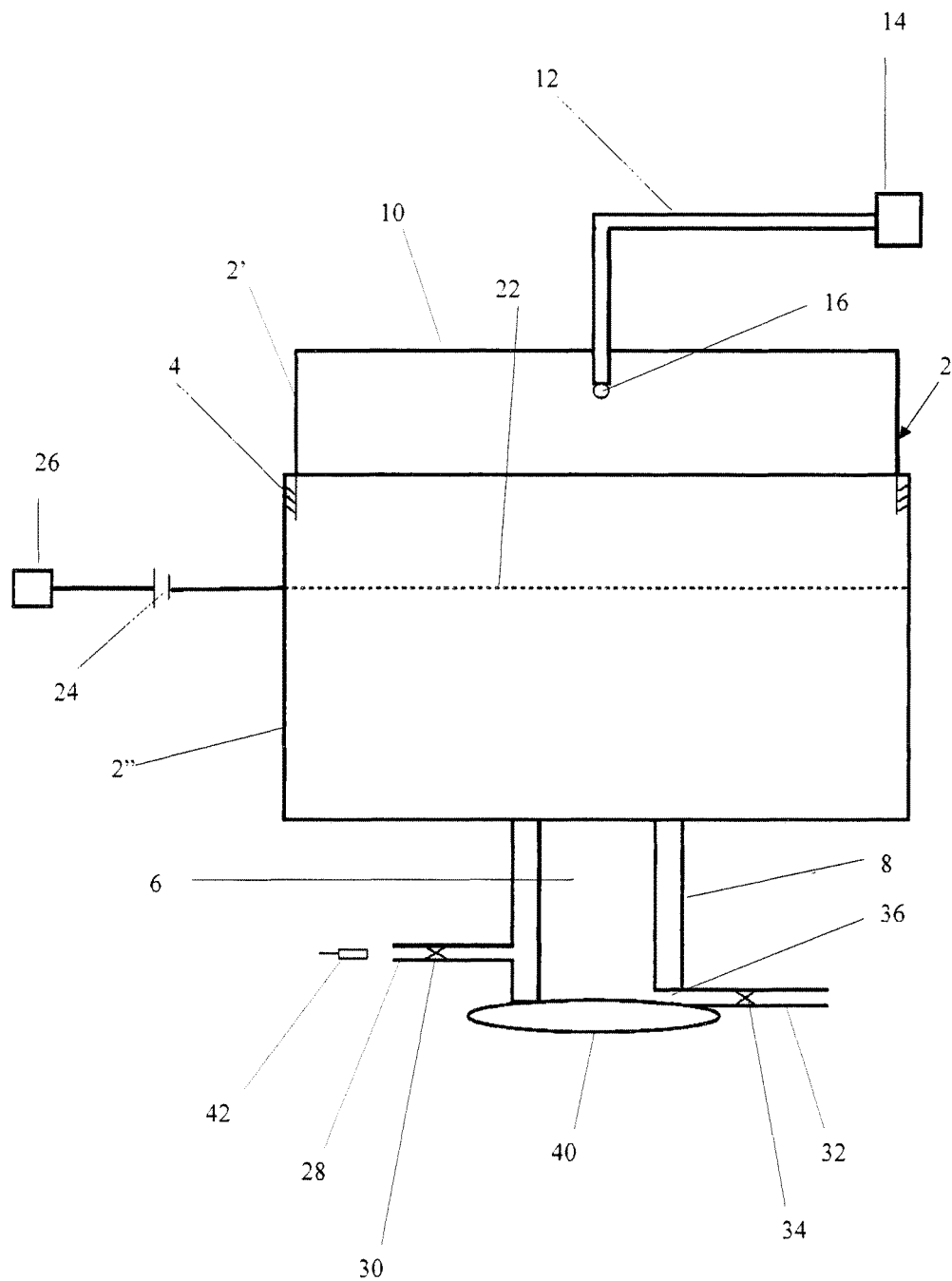

OPHTHALMOLOGICAL DEVICE FOR THE TREATMENT OF KERATOCONUS

This invention concerns an ophthalmological device for the treatment of keratoconus.

Keratoconus is a bilateral degenerative disorder of the eye that progressively thins and deforms the cornea making it more conical shape than that of its normal curvature. The cornea of the eye becomes thinner with a consequent reduction of rigidity and stability. This usually results in a substantial impairment of vision and corneal scarring.

As a result of the pressure inside the eye, the weakening of the cornea leads to bulging eyes, which in turn make the eye ametropic.

Therefore, there is an additional risk of ametropia that becomes more dangerous if the disorder is not treated effectively.

It was found that the crosslinking of the collagen fibres of the cornea can increase the stiffness of the cornea so that it can better the resist internal pressure of the eye. For this purpose it is known to use a photosensitizer such as riboflavin or a riboflavin solution which is applied to the eye.

This photosensitizer is able, under the influence of photons, to react chemically with the corneal tissue. After the riboflavin has been absorbed by the eye, it is subjected to UV radiation. Following the UV radiation the photosensitizer induces a crosslinking of the collagen fibres, thus increasing the biomechanical elasticity of the cornea, so that the cornea is less easily deformed under the influence of the pressure of the eye.

For this purpose, ocular iontophoresis devices have been proposed to transfer a drug such as a riboflavin solution to the cornea. This known device comprises a reservoir containing a riboflavin solution, suitable to be placed on the eye, an active electrode arranged on the reservoir, a passive electrode suitable to be placed on the skin of the subject, preferably in the vicinity of the eye, and means for irradiating the surface of the cornea with UV light, to obtain the corneal crosslinking after administration of the drug. The active electrode is transparent to ultraviolet rays and to visible and infrared light.

However, this device has the drawback that, since during the treatment with UV rays the corneal surface tends to dry out, as a consequence, an operator is needed to continuously bathe the corneal surface during UV application.

WO2012095876 describes a device and a method for corneal riboflavin administration for iontophoresis.

US20090069798 describes a method for cooling the corneal surface to minimize heat-related damage during thermokeratoplasty The purpose of the invention is to provide a device that allows for the ocular surface to be continuously kept wet.

All of these purposes and others which will be apparent from the description which follows are achieved according to the invention with an ophthalmological device for the treatment of keratoconus as described in claim 1.

This invention is further clarified here below with reference to the attached FIG. 1 of drawings representing a schematic view of the device according to the invention.

As can be seen from the FIGURES, the device according to the invention substantially comprises a reservoir 2 in cylindrical form made of electrically non-conductive material, preferably plastic.

The reservoir 2 is formed by two portions, 2' and 2" respectively, telescopically engaged together by means of a threaded portion 4. The lower portion 2" features an open bottom adjoining with a cylindrical chamber 6 of smaller diameter open at the bottom, to which an external annular chamber 8 is concentrically arranged, closed at the top and this is also open at the bottom. The upper portion 2' is provided with a support 10 of an optical fibre 12 which is fed by a UV source 14 and is provided, at the end housed inside the reservoir 2, with a lens system 16.

Inside the lower portion 2" a horizontal metal grid 22 is housed, connected through a terminal conductor of a DC current generator 24 from 0.5 to 3 mA to which other terminal an electrode 26 is connected preferably applicable on the forehead or laterally to the eye of the patient.

The device also comprises a conduit 28 with closing valve 30 that flows into the annular chamber 8 and a conduit 32, with a closing valve 34, which passes through the annular chamber 8 in correspondence with its lower edge and whose open end 36 is connected with the chamber 6.

The operation of the device according to the invention is as follows.

The reservoir 2 is placed on the eye 40 of the patient in correspondence with the lower edge of the annular chamber 8. The valve 34 is closed and the valve 30 is opened and then the vacuum is applied, by means of a syringe 42 introduced into the conduit 28, in such a way that the annular chamber 8 provides sealed adherence to the eye itself. After closing the valve 30 the valve 34 is opened and, via the conduit 32, a predetermined quantity of riboflavin is injected. Subsequently, after closing the valve 34, the generator 24 is switched on creating a current flow that diffuses ions of riboflavin across the epithelium of the cornea.

At the end of the treatment, the valve 34 is opened to release the residual ion-poor riboflavin and source 14 is activated which, through the lens system 16 of the optical fibre 12, causes the cross-linking of the riboflavin absorbed by the corneal tissue. This crosslinking allows the reinforcement of the structure of the cornea affected by keratoconus and increases the connection between the fibres and the corneal collagen. In this phase it is possible to adjust the distance of the LED 16 by rotating the portion 2' in one direction then the other with respect to the lower portion 2"

It should be noted that since the optical fibre 10 is soft and pliable, excessive mechanical stress is avoided on the eye during the treatment.

During the irradiation phase, a hydrating solution is administered from above through the grid holes 22 that touches the eye and is released through the conduit 32 so as to avoid the excessive absorption of incident energy by the hydrating solution while maintaining a minimum thickness and constant hydrating solution on the ocular surface.

The constant wetting of the corneal epithelium prevents it from being damaged as a result of drying.

It is necessary to maintain a uniform hydrated film with a minimum constant thickness for the uniformity and efficiency of the crosslinking. This can be conveniently achieved by adjusting the size of the opening 36.

The technical data of the device can be as follows:
max outer diameter 12 mm
lighting surface (diameter) min 1 mm, max 10 mm
distance of the light source from the corneal surface: min 1 mm, max 20 mm, nominal 10 mm
wavelength of the illuminating surface: UV-4 315 nm-400 nm and visible 400-800 nm
power of the light source min 1 mW/cm$^2$ to 250 mW/cm$^2$
energy (power×time) or flow: 1 J/cm$^2$ to 150 J/cm$^2$.

In case riboflavin is used as photosensitizer the wavelength may be 365 nm and the energy 5.4 J/cm$^2$ If using Rose Bengal as photosensitizer the light source can be 532 nm, flow 150 J/cm$^2$ flow rate for hydrating solution: 10 to 100 μl/min
corneal radius: 7.8 mm+/−0.5 mm corneal thickness: min 300 nm-max 600 nm (at the centre).

In an alternative variant not shown in the drawings, a diaphragm is also provided inside the reservoir with a plurality of holes so as to allow a partial irradiation.

The invention claimed is:

1. Ophthalmological device for treatment of keratoconus, comprising:
   a cylindrical reservoir made of a non-conductive material with an open bottom, said reservoir being formed by a lower portion (2") and an upper portion (2') telescopically engaged together, said reservoir being fed during use from above with a hydrating solution,
   a cylindrical chamber (6) of smaller diameter than the cylindrical reservoir and adjoining said reservoir at the open bottom of said lower portion (2"), said cylindrical chamber (6) being open at a bottom,
   an external annular chamber (8) concentrically arranged around said cylindrical chamber (6) and closed at a top and open at a bottom,
   a first metallic conductor (22), housed in the lower portion (2") of the cylindrical reservoir, connected to a terminal of a DC voltage generator (24), to another terminal of which a second metallic conductor (26) is connected,
   a first conduit (28) provided with a closing device (30), one end of said conduit flowing into the annular chamber (8), another end of said conduit being adapted to be connected to a vacuum source, and
   a second conduit (32) provided with a closing device (34), one end of said second conduit passing through said annular chamber (8) at a lower edge thereof and flowing into the cylindrical chamber (6), another end of said second conduit being located externally to the said annular reservoir (8) for discharging the hydrating solution.

2. The Ophthalmological device according to claim 1, wherein the first conductor comprises a circular grid (22) arranged horizontally in the lower portion of the cylindrical reservoir.

3. The ophthalmological device according to claim 1, further comprising an optical fiber (12) mounted on a support (10) disposed in the upper portion (2') of the cylindrical reservoir, an end of said optical fiber being housed inside said upper portion and being provided with a lens system (16).

* * * * *